United States Patent [19]

Unruh et al.

[11] 4,139,565
[45] Feb. 13, 1979

[54] HYDROFORMYLATION USING IMPROVED CATALYSTS COMPRISING RHODIUM AND DIPHOSPHINO LIGANDS

[75] Inventors: Jerry D. Unruh; Leslie E. Wade, both of Corpus Christi, Tex.

[73] Assignee: Celanese Corporation, New York, N.Y.

[21] Appl. No.: 783,121

[22] Filed: Mar. 31, 1977

[51] Int. Cl.$^2$ ............................................. C07C 45/08
[52] U.S. Cl. ............................................. 260/604 HF
[58] Field of Search ......... 260/604 HF, 429, 632 HF; 568/909

[56] References Cited

U.S. PATENT DOCUMENTS

| | | | |
|---|---|---|---|
| 3,239,566 | 3/1966 | Slaugh et al. | 260/604 HF |
| 3,527,809 | 9/1970 | Pruett et al. | 260/604 HF |

FOREIGN PATENT DOCUMENTS

| | | | |
|---|---|---|---|
| 840906 | 10/1976 | Belgium | 260/604 HF |
| 1402832 | 7/1975 | United Kingdom | 260/604 HF |
| 1452196 | 10/1976 | United Kingdom | 260/604 HF |

Primary Examiner—James O. Thomas, Jr.
Assistant Examiner—Werren B. Lone
Attorney, Agent, or Firm—Ralph M. Pritchett

[57] ABSTRACT

In hydroformylating an ethylenically-unsaturated compound to produce a formyl-substituted derivative using as catalyst rhodium hydrido carbonyl in complex combination with a disphosphino ligand, a high ratio of the normal aldehyde to the iso-aldehyde in the product can be obtained even at very low ratios of ligand to rhodium in the catalyst mixture by using as the ligand a cyclic compound having in the ring two adjacent carbon atoms between the trans position of which the minimum and maximum attainable dihedral angels are, respectively, at least about 90° and not more than about 180°, each of these adjacent carbon atoms being substituted with a phosphinomethyl group, the phosphinomethyl groups being in trans relationship to one another. If there are maintained in the reaction zone at least about 1.5 moles of the ligand per atom of rhodium, the desired results are obtained and higher ligand:rhodium ratios are not necessary.

4 Claims, 1 Drawing Figure

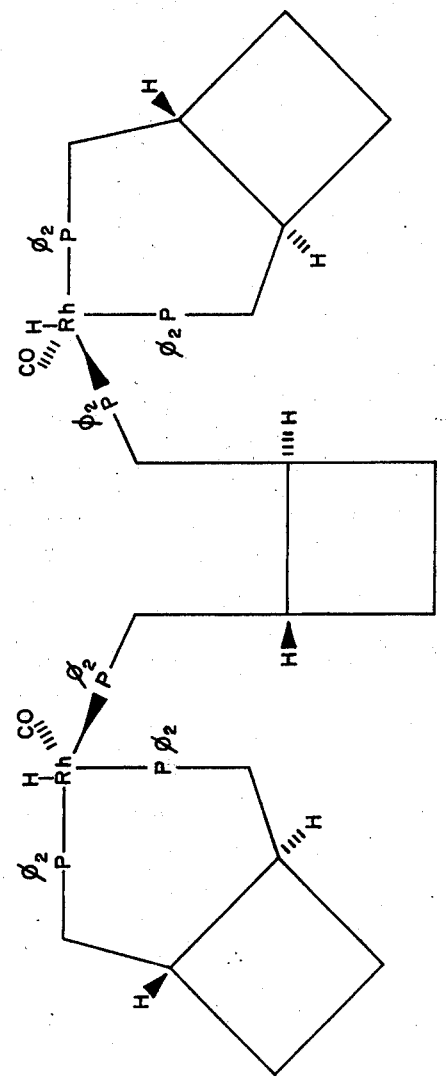

HYDROFORMYLATION USING IMPROVED CATALYSTS COMPRISING RHODIUM AND DIPHOSPHINO LIGANDS

BACKGROUND OF THE INVENTION

Hydroformylation of an olefin to produce a formyl-substituted derivative of the olefin is now well-known in the art as an economically attractive method for producing, in particular, the aldehydes which are the primary intermediates in the manufacture of, for example, alkanols such as n-butanol and the corresponding alkanoic acids. Also important are such end products as 2-ethylhexanol, which is formed from n-butyraldehyde by a sequence of steps including aldoling, dehydration, and hydrogenation by methods which are well-established in the art.

While hydroformylation processes using cobalt carbonyl as the major component of the catalyst have been known and used for many years, systems in which the catalyst comprises rhodium hydrido carbonyl complexed with an organic ligand have been developed more recently and are now favored over the older technology for several reasons including the fact that they can be used under relatively mild reaction conditions and also, of very great importance, the fact that the rhodium-catalyzed systems can be controlled so as to yield a product in which the normal isomer of the aldehyde predominates over the branched-chain isomer to a greater extent than has normally been obtained heretofore when using the older methods. It will be understood in this connection that for most industrial purposes, including use as a raw material for production of the corresponding alkanoic acids (by catalytic oxidation of the aldehyde) and also for the production of higher molecular weight alcohol derivatives (as by aldoling etc.), the normal aldehyde is strongly preferred over the branched-chain isomer. In the case of the butyraldehydes, for example, n-butyraldehyde finds a ready and expanding market whereas isobutyraldehyde has fewer uses and is considered an undesirable by-product. Similarly, in the case of longer-chain aldehydes such as heptaldehyde, the normal isomers can be used to produce high-quality ester-type synthetic lubricants, while the properties of the corresponding branched-chain isomers are such that they have little value for such purposes.

Use of the rhodium-containing catalyst systems results in the attainment of an improved normal:iso ratio in the aldehyde products formed in these processes (as compared with the cobalt-based systems), but formation of the branched-chain isomer continues to be a significant economic drawback. By controlling such parameters as carbon monoxide partial pressure, carbon monoxide:hydrogen ratio, etc. it is possible to influence the product distribution somewhat in a favorable direction. A very significant process parameter is also the ratio of ligand to rhodium in the catalyst mixture, it having been discovered that the normal:iso ratio in the product increases with increasing ligand:rhodium ratio. For example, phosphine-type ligands, including specifically and for example triphenylphosphine, are customarily employed in rhodium-catalyzed hydroformylation systems in proportions such that the ratio of phosphorus to rhodium is at least about 10:1, ranging on upwardly to as much as 1000:1. Ratios lower than about 2:1 have been found to be distinctly unsatisfactory. As the phosphorus:rhodium ratio is increased in the systems employing the previously-recognized ligands such as triphenylphosphine, there is a gradual improvement in the normal:iso ratio in the product aldehydes indicative of an equilibrium-type reaction. Thus, normal practice is to use a substantial excess of ligand on the basis of judgment and various experience factors including, for example, practical observation of the rapidity of catalyst deactivation observed with various ligand:rhodium ratios.

The state of the existing art in the field of hydroformylation of olefins using as catalysts rhodium hydrido carbonyl complexed with organic ligands, including particularly phosphines and also phosphites, is exemplified by U.S. Pat. No. 3,239,566 to Slaugh and also U.S. Pat. No. 3,527,809 to Pruett et al. as well as U.S. Pat. No. 3,511,880 to Booth. These patentees describe hydroformylation processes in which, by using a complexed Group VIII noble metal, and particularly rhodium, the high pressures required in the cobalt carbonyl-catalyzed reaction systems are avoided while attractive ratios of normal aldehyde to branched-chain aldehyde are also obtained in the products. The ligands employed, however, as exemplified by triphenylphosphine, are used in a substantial excess. That is, as will be seen from examining the disclosures of these and similar related prior-art references, at least about 2 moles of the ligand are used per atom of rhodium. Also, continuing research in these reactions has indicated that, with these prior-art ligands, there is no ligand:rhodium ratio (up to compositions in which the entirety of the reaction medium comprises ligand) above which the addition of more of the ligand ceases to have an effect on product distribution.

More recently it has been discovered, as disclosed in Belgian Pat. No. 840,906 (Oct. 20, 1976), that the nature of the ligand in these reaction systems is a more significant factor than has been recognized heretofore. More particularly, it has been discovered that certain bidentate ligands which are derivatives of ferrocene are capable, in catalytic complexes with rhodium, of yielding hydroformylation product mixtures in which there is an unusually high ratio of normal isomer to branched-chain isomer without the requirement of employing a high ratio of ligand to rhodium in the catalyst. Furthermore, with these ferrocene-based ligands (which include specifically diphosphino-substituted ferrocenes) there is little need for maintaining in the reaction zone more than about 1.5 moles of the ferrocene derivative per atom of rhodium (a phosphorus:rhodium mole ratio of 3.0:1). Insofar as the teachings of Belgian No. 840906 are concerned, however, the ligands reported therein require the presence of the ferrocene moiety.

The use of bidentate diphosphino ligands is also disclosed in British Pat. No. 1,402,832, to Pino, wherein it is disclosed that asymmetric hydroformylation of olefinically unsaturated prochiral compounds can be accomplished by carrying out the hydroformylation in the presence of an optically active diphosphino compound, with the recommended diphosphino compounds including certain bis-(diphenylphosphinomethyl) compounds. The thrust of British Pat. No. 1,402,832 is in the direction of obtaining optically active aldehyde products. There is no teaching of any benefit from using optically inactive ligands of this general type, nor of any advantage of such compounds, whether optically active or not, as ligands in relation to such factors as normal:iso aldehyde distribution in the reaction product.

3

It is an object of the present invention to provide a family of bidentate ligands for use in rhodium-catalyzed hydroformylation processes which do not require optical activity for their efficacy and which need not be employed, in the reaction system, at the high ligand:-rhodium ratios characteristic of the related prior art. It is another object to provide an improved hydroformylation process for converting an ethylenically-unsaturated raw material to a formyl-substituted derivative thereof wherein the ratio of normal aldehyde to branched-chain aldehyde in the reaction product is of a high, economically-attractive level without the necessity of using stringent reaction conditions nor a high excess of ligand. Other objects will be apparent from the following detailed description.

SUMMARY

In accordance with the present invention an ethylenically-unsaturated feedstock is converted to an aldehyde derivative having one carbon atom more than the parent feedstock by hydroformylation with hydrogen and carbon monoxide in a reaction zone containing a liquid-phase reaction medium which contains a hydroformylation catalyst composed of rhodium hydrido carbonyl in complex combination with a diphosphino-substituted ligand. The diphosphino-substituted ligand is an optically-inactive cyclic compound having in the ring two adjacent carbon atoms between the trans positions of which the minimum and maximum attainable dihedral angles are, respectively, at least about 90° and not more than about 180°. Each of the adjacent carbon atoms just referred to is substituted with a phosphinomethyl group, with the phosphinomethyl groups being in trans relationship to one another. The presence of optically active ligand moieties is not deleterious, but optical activity serves no useful purpose in affecting chemical efficiency, normal:iso aldehyde ratio, etc.

Particularly useful ligands are those in which both phosphinomethyl groups are dihydrocarbylphosphinomethyl, especially diphenylphosphinomethyl groups.

It is strongly recommended that the catalyst contain at least about 1.5 moles of the diphosphino-substituted ligand per atom of rhodium, under which conditions the evidence at hand indicates that there is actually formed a complex catalyst molecule comprising two atoms of rhodium and three moles of the ligand. Maintaining a ligand:rhodium ratio greater than about 1.5:1 is not necessary although not in any way deleterious.

The product comprises the normal aldehyde and the branched-chain aldehyde in a normal:iso ratio which is quite high and which, under otherwise comparable reaction conditions of pressure etc., can be approached in catalyst systems using the ligands characteristic of the prior art only if the prior-art ligands are used in a very substantial excess over the rhodium.

DETAILED DESCRIPTION AND PREFERRED EMBODIMENT

Of the ligands the use of which is central to the present process, there is one, i.e., trans-1,2-bis(diphenylphosphinomethyl)cyclobutane, which in the optically-active form as distinguished from the optically inactive form, is mentioned in British Pat. No. 1,452,196 (to Rhone-Poulenc) as being a component of hydrogenation catalysts which comprise ligand and a rhodium halide, the patent being directed to the hydrogenation (not hydroformylation) of a substituted acrylic acid or acrylate ester to form an optically-active product. Although said British Pat. No. 1,452,196 does not deal with hydroformylation and does not identify the broad structural characteristics of suitable ligands which have now been found to be correlatable with the attainment of high normal:iso ratios in the product of hydroformylation reactions, the patent is pertinent to the present disclosure in that (a) it discloses one use of a ligand of the present type and also (b) it sets forth methods whereby the present ligands can be synthesized. It will be seen that, although British Pat. No. 1,452,196 employs a bis-(1,2-hydroxymethyl)cyclobutane as the starting material for synthesis of the 1,2-bis(diphenylphosphinomethyl)cyclobutane which is the ligand employed therein, analogous dihydroxymethyl-substituted compounds of other cyclic structures can be used as raw materials for synthesizing the other diphenylphosphinomethyl-substituted ligands which can also be employed in the present process.

The properties which the present class of ligands have in common and which are essential to their efficacy in the present process are the following:

(1) First is a skeleton structure which holds two phosphorus atoms of the ligand at an interatomic distance which is particularly favorable to the formation of a stable and selective catalytic complex with rhodium hydrido carbonyl.

(2) Second, the phosphorus atoms in the ligand molecule must be free to rotate. This is for the reason that the present catalytic complexes, when sufficient ligand is present to provide 1.5 moles of the bidentate ligand per atom of rhodium, comprise two rhodium atoms which are connected to one another by one of the ligand molecules (i.e., a bridging molecule), with each of these rhodium atoms then being, in addition, complexed with another mole of the ligand. The bridging mole of ligand must, then, have its phosphorus atoms free to rotate so that it can perform this bridging function between the two rhodium atoms each of which is already complexed in a chelate structure with a mole of the ligand. An example of this structure is illustrated in the drawing, which shows the complete catalytic complex which is formed when using as the ligand 1,2-bis(diphenylphosphinomethyl)cyclobutane. It should be pointed out that the drawing shows the chelate bonded axial-equatorial to the rhodium, but it is equally satisfactory for the bonding to be equatorial-equatorial.

It will be understood that the ring structure need not necessarily be cyclobutane. Any other ring which can provide two adjacent carbon atoms in proper relationship to one another can be employed as will be further explained hereinbelow.

Optical activity in the ligands does not, per se, frustrate the purposes of the present process, but it is in no way necessary since the optically-inactive forms (including the racemic modification specifically) are entirely satisfactory and are much easier to obtain. Thus, for example, a racemic modification containing an additional admixture of one of the optical isomers such that the mixture has optical activity is equivalent to the optically inactive racemic modification for present purposes but the optical activity is in no way ncessary.

From the foregoing it will be seen that further explanation of the role of the methylene group connecting the phosphino moiety with the ring is not necessary. Simply, its function is to provide rotatability for the phosphorus atom and its attached substituent groups so that the complete catalytic complex can be readily formed.

Regarding the ring structure, and the two adjacent carbon atoms within it which are essential to the formation of the present complexes:

First, the presence of a ring is called for solely for the reason that such a structure provides a framework which, because of the steric conformations available to it, can hold two adjacent carbon atoms in the requisite spatial relationship to one another whereby, after they have each been substituted with a dihydrocarbylphosphinomethyl group, the two phosphorus atoms which are so incorporated into the molecule will be so spaced in regard to each other that the present improved rhodium complexes are readily formed. Otherwise, the presence of a ring, qua ring, is not relevant.

Second, the ring must be one within which the two adjacent carbon atoms which are substituted with dihydrocarbylphosphinomethyl groups to form the present ligands have, between their trans positions, a dihedral angle which is not less than about 90° and not greater than about 180°. A dihedral angle much less than 90° will position the two phosphorus atoms of the ligand too closely to one another for ready chelation of the rhodium atom. Likewise, a dihedral angle much greater than 180° will result in too great a distance between the phosphorus atoms for optimum chelation effectiveness. These factors mean that the ring must be one which restricts the spatial relationship between the two phosphinomethyl-substituted carbon atoms. For example, the cyclobutane ring and the cyclopentane ring are comparatively rigid and are suitable for present purposes. The cyclohexane ring, however, has steric characteristics such that the carbon atoms contained within it can rotate readily with the result that the dihedral angle of the trans positions between any two adjacent carbon atoms can be varied easily between 0° and 180°. The cyclohexane ring, then, is not suitable for present purposes.

It will also be understood that a given ring structure may be capable of existing in more than one conformation. For present purposes this is not relevant so long as, whatever the nature of the available conformations may be, they do not include one in which the dihedral angle between the trans positions of the two adjacent phosphinomethyl-substituted carbon atoms can be less than about 90° nor more than about 180°.

While it is possible to make geometrical calculations of the dihedral angle in a given cyclic molecule in order to determine whether it fits the present requirements, it is preferable, and simpler, to make use of three-dimensional molecular models, manipulating them into all their spatial conformations and, by direct observation, testing whether the dihedral angle in question remains between 90° and 180°. For this purpose one can use "ball-and-stick" models or, more preferably, "skeletal" models of the type in which the carbon atom is represented by a caltrop-like structure formed by four rods radiating from a central juncture.

While the cyclic moiety from which the present ligands are derived will normally be composed of carbon and hydrogen, the presence of other a atoms can be allowed so long as there are still present within the ring two adjacent carbon atoms which fulfill the requirement that the dihedral angle between their trans positions be between about 90° and about 180° as previously explained. Normally, however, the cyclic compound which is substituted with the two phosphinomethyl moieties to form the present ligand will be free of atoms other than carbon, hydrogen, and oxygen.

Although in the preferred ligands the parent cyclic compound is substituted with two diphenylphosphinomethyl groups:

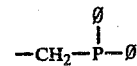

It is also within the scope of the invention to employ dihydrocarbylphosphinomethyl groups of the formula:

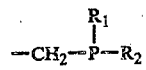

in which $R_1$ and $R_2$ are either alike or different and are either (a) aryl (preferably phenyl), aralkyl, or alkaryl groups or else (b) lower alkyl groups, of up to about 12 carbon atoms.

Particularly preferred ligands for use in the present process are the following:
trans-1,2-bis(diphenylphosphinomethyl)cyclopropane
trans-1,2-bis(diphenylphosphinomethyl)cyclobutane;
trans-1,2-bis(diphenylphosphinomethyl)cyclopentane;
trans-9,10-bis(diphenylphosphinomethyl)-9,10-dihydrophenanthrene;
trans-1,2-bis(diphenylphosphinomethyl)-trans-decalin;
trans-2,3-bis(diphenylphosphinomethyl)-trans-decalin; and
trans-1,9-bis(diphenylphosphinomethyl)-trans-decalin.

Of the foregoing, the trans-1,2-bis(diphenylphosphinomethyl)cyclobutane in particular is quite effective and readily attainable by straight-forward methods.

The olefinically unsaturated feedstock which is to be hydroformylated by the present improved process can be any of the many types of olefin already known in the art to be suitable for rhodium-catalyzed hydroformylations, especially olefinic compounds having in the molecule up to about 25 carbon atoms. Although mono-unsaturated compounds are normally employed and of particular practical importance, di- and triethylenically unsaturated olefins can also be used, the product in each case being, if complete hydroformylation is carried out, a derivative having up to one additional carbon atom for each ethylene double bond in the parent compound. Olefinic compounds having substituted groups, e.g., ethylenically-unsaturated alcohols, aldehydes, ketones, esters, carboxylic acids, acetals, ketals, nitriles, amines, etc. can be easily hydroformylated as well as the simple mono-alkenes which are particularly useful and of particular commercial importance. Broadly, ethylenically-unsaturated compounds which are free of atoms other than carbon, hydrogen, oxygen, and nitrogen are readily hydroformylated, and more particularly compounds consisting solely of oxygen, hydrogen, and carbon. Some specific classes of substituted olefins to which the hydroformylation process is applicable are: unsaturated aldehydes such as acrolein and crotonaldehyde; alkenoic acids such as acrylic acid; and unsaturated acetals, such as acrolein acetal. More commonly, suitable hydroformylation feedstocks include the simple alkenes such as ethylene, propylene, the butylenes, etc.;

alkadienes such as butadiene and 1,5-hexadiene; and the aryl, alkaryl, and aralkyl derivatives of the foregoing. Lower mono-alkenes of 2 to about 12 carbon atoms are especially useful. Hydroformylation does not normally take place within the benzene ring of olefins having aryl substitution, of course, but rather in the ethylenically-unsaturated portion of the molecule.

Process operating parameters to be employed in practicing the present process will vary depending upon the nature of the end product desired, since, as already known in the art, variation of operating conditions can result in some variation in the ratio of aldehydes to alcohols produced in the process (some alcohol may be formed in small amounts along with the aldehyde which is normally the desired product) as well as the ratio of the normal to the branched-chain aldehyde derivative of the parent feedstock. The operating parameters contemplated by the present process are broadly the same as those conventionally employed in hydroformylation processes using rhodium complexes as already known in the art. For the sake of convenience, these parameters will be generally set forth hereinbelow; it being understood, however, that the process parameters are not critical to achieving the improved results of the present invention as compared with processes using the prior-art ligands and do not, per se, form a part of it. That is, the present improvement lies in the use of the present improved ligands and not in the concomitant employment of any change from existing rhodium hydroformylation technology as already known to the art. To repeat the point, using the present improved catalyst system does not necessitate any departure from rhodium-catalyzed hydroformylations as already known, except for changing the ligand.

In general, the hydroformylation process is conducted under a total reaction pressure of hydrogen and carbon monoxide combined of one atmosphere or even less, up to a combined pressure of about 700 atmospheres absolute. Higher pressures can be employed but are normally not required. For economic reasons, however, pressures significantly greater than about 400 atmospheres absolute will not normally be employed.

The reaction is normally conducted at a temperature of from about 50° to about 200° C., with a temperature within the range of about 75° C. to about 150° C. being most commonly employed.

Unlike the prior art, a substantial excess of ligand in proportions to the rhodium is not required although it is not harmful. More specifically, it is desirable to employ at least about 1.5 mole of the present bidentate ligands per atom of rhodium, but so long as sufficient ligand is present to insure the maintenance of at least this ratio (which can also be defined as 3 atoms of phosphino phosphorus per atom of rhodium) there is no need to provide additional ligand. As previously explained, experience with these ligands indicates that, once the 1.5:1 ratio is attained, the catalyst complex as depicted in the drawing is formed and additional quantities of ligand have no further effect although there is no adverse effect on performance of the system.

The ratio of partial pressures of hydrogen to carbon monoxide in the reaction vessel may be from about 10:1 to about 1:10 in accordance with the prior art, although it has been discovered that when using the present ligands this range may even be extended to about 50:1 to 1:50. Normally, however, the range of hydrogen partial pressure to that of carbon monoxide will be from about 6:1 to about 1:1, with a hydrogen:carbon monoxide ratio of about 1:1 usually being employed.

As is also known from the prior art, a liquid reaction medium is employed. Frequently, and most commonly, this can be the ethylenically unsaturated feedstock itself. A separately-added solvent can be employed if desired, however, particularly when the feedstock is of high volatility such that maintaining a liquid phase would require maintenance of excessive pressure under the reaction temperature which is to be employed. When the solvent is to be a liquid other than the olefinic reactant or a product of the hydroformylation process, it is preferred that it be one which is inert toward the catalyst and reactants under conditions obtaining within the reaction zone. Suitable reaction solvents include: benzene, toluene, diphenyl ether alone or mixed with biphenyl, esters, polypropylene oxides, ketones, aldehydes, ethylene glycol, alkanes, alcohols, and lactones.

Whatever may be the composition of the liquid reaction medium (i.e., whether it comprises predominantly a separate reaction solvent or the ethylenically unsaturated feedstock itself), the catalyst complex should be maintained in it at a concentration of about 0.1 to 50 millimoles/l calculated as rhodium. More preferably, about 1.0 to 20.0 millimoles/l of rhodium is recommended. While the catalyst can be formed ex-situ, it is conveniently prepared in-situ in the liquid reaction medium by introducing the ligand along with a suitable rhodium source and then allowing complexation to occur under the temperature to be employed in the hydroformylation reaction and in the presence of the hydrogen:carbon monoxide gas mixture which is to be used in the hydroformylation process. A suitable rhodium source is $HRh(CO)(P\varnothing_3)_3$. Other rhodium sources which can be used include: rhodium on carbon, $Rh_2O_3$, $Rh(NO_3)_3$, $Rh_2(SO_4)_3$, $RHCl_3.3H_2O$, $RhClCo(P\varnothing_3)_2$, $[Rh(CO)_2Cl]_2$ $[Rh(1,5-cyclooctadiene)Cl]_2$, $RhBr_3$, and $RhI_3$. If a halogen-containing rhodium source is to be employed, it is desirable to include with it a sufficient quantity of an alkaline reactant (e.g., sodium hydroxide) to scavenge the halide moiety out of the system as the complex is formed.

The following Examples are given to illustrate the preferred practice of the invention and also to illustrate the effect of catalyst concentration, hydroformylation reaction pressure, and hydrogen:carbon monoxide ratio. It will be understood that many variations can be made, in accordance with the explanations given hereinabove and in the light of hydroformylation technology as already known in the existing art:

EXAMPLE 1

A 300 ml stirred stainless steel autoclave was charged with 60 ml of toluene as inert reaction solvent, 0.1 millimole of rhodium as $HRh(CO)(P\varnothing_3)_3$, and the desired amount of ligand, which was, in this as well as in the following examples, 1,2-bis(diphenylphosphinomethyl)-cyclobutane. The autoclave was then closed and flushed several times with a 1:1 mixture of hydrogen and carbon monoxide. The autoclave was then pressured to about 1.3 atmospheres gauge with the 1:1 hydrogen:carbon monoxide mixture, after which the autoclave was raised to the desired reaction temperature which, in this example, was between 108° C. and 112° C. Next, 20 ml of 1-hexene, which had been preheated to reaction temperature, was pressured into the autoclave from a reservoir which was pressured by 1:1 synthesis gas. Additional 1:1 synthesis gas was then admitted into the autoclave from an external reservoir (which was maintained continuously at a pressure higher than that of the autoclave) so as to attain in the autoclave a reaction pressure of from about 96 psig to 106 psig.

Upon attainment of the desired set autoclave reaction pressure, the run was taken as having been started, and thereafter the rate of reaction was monitored by continuously observing the rate at which the pressure in the external synthesis gas reservoir declined as the contained gas was consumed in the reaction autoclave.

When the rate of reaction had dropped to an extremely low level, as indicated by a very low rate of decline of the synthesis gas reservoir pressure, the autoclave was cooled to ambient temperature and its contents were removed and analyzed chromatographically. The results, as shown in Table I, showed clearly that a sharp increase in catalyst effectiveness took place as the ligand:rhodium mole ratio was raised up to 1.5:1. Additional increase in the ratio above 1.5:1 was found to have but little effect on the progress of the reaction.

The results, as shown in Table II below, indicate that the efficiency to aldehydes was nearly independent of reaction pressure so long as the pressure was at least about 50 psig. By-products such as hexane and 2-hexene were a minor proportion of the reaction product so long as the reaction pressure was above 50 psig. Reaction rate, however, declined with increasing reaction pressure.

TABLE II
EFFECT OF REACTION PRESSURE

| | Run No. | | | | | | | | |
|---|---|---|---|---|---|---|---|---|---|
| | 24693-35 | 24693-34 | 24693-26 | 24693-27 | 24693-28 | 24693-29 | 24693-30 | 24693-32 | 24693-36 |
| Rhodium, millimoles | 0.1 | 0.1 | 0.1 | 0.1 | 0.1 | 0.1 | 0.1 | 0.1 | 0.1 |
| Ligand, millimoles | 0.2 | 0.2 | 0.2 | 0.2 | 0.2 | 0.2 | 0.2 | 0.2 | 0.2 |
| Ligand-rhodium mole ratio | 2.0 | 2.0 | 2.0 | 2.0 | 2.0 | 2.0 | 2.0 | 2.0 | 2.0 |
| Pressure, psig (1:1, $H_2$:CO) | 49–53 | 75–80 | 98–106 | 99–107 | 99–105 | 146–152 | 148–151 | 197–202 | 298–303 |
| Ratio of n- to iso-aldehyde in product | 6.25 | 6.82 | 6.99 | 6.83 | 6.92 | 7.06 | 7.08 | 7.07 | 7.14 |
| 1-Hexene conversion, % | 99.9 | 99.9 | 99.9 | 99.9 | 99.9 | 99.9 | 99.4 | 99.7 | 99.6 |
| $k_{obs}$, min$^{-1}$ | 0.144 | 0.118 | 0.126 | 0.159 | 0.122 | 0.085 | 0.058 | 0.069 | 0.056 |
| Percent of reacted hexene converted to: | | | | | | | | | |
| heptanal | 82.07 | 85.06 | 85.80 | 85.48 | 86.01 | 86.35 | 86.33 | 86.56 | 86.59 |
| 2-methylhexanal | 13.13 | 12.48 | 12.28 | 12.51 | 12.44 | 12.22 | 12.19 | 12.24 | 12.14 |
| 2-hexene | 3.58 | 1.66 | 1.37 | 1.40 | 1.01 | 0.85 | 0.86 | 0.73 | 0.78 |
| hexane | 1.23 | 0.80 | 0.55 | 0.61 | 0.54 | 0.51 | 0.62 | 0.48 | 0.50 |

EXAMPLE III

Apparatus and procedures were the same as in Examples I and II above, except that the composition of the hydrogen:carbon monoxide synthesis gas was varied between 1:1 and 4:1. The ligand:rhodium ratio was 2.0 in all cases and reaction temperature was approximately 110° C. in all cases, as in Example II. The carbon monoxide partial pressure was maintained substantially constant throughout the entire series of runs, but the total pressure varied from 102 up to 251 psig as the proportion of hydrogen was increased. Total pressure varied

TABLE I
EFFECT OF VARIATION IN LIGAND:RHODIUM RATIO

| | Run No. | | | | | |
|---|---|---|---|---|---|---|
| | 24693-25 | 24693-24 | 24693-23 | 24693-22 | 24693-26,27,28 | 24693-21 |
| Rhodium, millimoles | 0.1 | 0.1 | 0.1 | 0.1 | 0.1 | 0.1 |
| Ligand, millimoles | 0.1 | 0.125 | 0.15 | 0.175 | 0.20 | 0.30 |
| Ligand, rhodium mole ratio | 1.0 | 1.25 | 1.50 | 1.75 | 2.0 | 3.0 |
| Ratio of n- to iso-aldehyde in product | 3.18 | 4.55 | 7.13 | 7.42 | 6.91 | 7.34 |
| 1-Hexene conversion, % | 99.9 | 99.9 | 99.9 | 99.9 | 99.9 | 99.9 |
| $k_{obs}$, min$^{-1}$ | 0.145 | 0.146 | 0.133 | 0.110 | 0.136 | 0.118 |
| Percent of reacted hexene converted to: | | | | | | |
| heptanal | 58.11 | 70.59 | 85.88 | 86.69 | 85.76 | 86.40 |
| 2-methylhexanal | 18.26 | 15.50 | 12.05 | 11.68 | 12.41 | 11.78 |
| 2-hexene | 23.21 | 13.46 | 1.37 | 1.17 | 1.26 | 1.31 |
| hexane | 0.43 | 0.45 | 0.49 | 0.46 | 0.57 | 0.51 |

Note:
In this and the following table, $k_{obs}$ is a pseudo-first order rate constant with respect to hexene.

EXAMPLE II

The same apparatus and procedure as outlined in Example I above were employed except that, as indicated in Table II below, the reaction pressure was varied from approximately 50 psig to approximately 300 psig. Reaction temperature, which was substantially the same in each run, was approximately 110° C. ± 2° C. The ligand:rhodium ratio was 2.0 in each run, for the purpose of insuring that there would be no danger of its being less than 1.5.

from 102 psig when the synthesis gas ratio was 1:1 up to 251 psig when the synthesis gas ratio was as shown.

The results presented in Table III below show that, at constant carbon monoxide partial pressure, the efficiency to the several reaction products was independent of hydrogen:carbon monoxide ratio but that the reaction rate decreased approximately eight fold on going from a hydrogen:carbon monoxide ratio of 1:1 up to a ratio of 2.0, after which the reaction rate remained substantially constant. This decline in reaction rate with increasing hydrogen:carbon monoxide ratio was unexpected.

TABLE III
EFFECT OF H₂:CO RATIO

|  | Run No. | | | |
| --- | --- | --- | --- | --- |
|  | 24693-26,27,28 | 24693-37 | 24693-38 | 24693-39 |
| Rhodium, millimoles | 0.1 | 0.1 | 0.1 | 0.1 |
| Ligand, millimoles | 0.2 | 0.2 | 0.2 | 0.2 |
| Ligand-rhodium mole ratio | 2.0 | 2.0 | 2.0 | 2.0 |
| Pressure, psig | 102.0±4.0 | 150±2.5 | 200.0±3.0 | 251.0±2.0 |
| H₂:CO ratio | 1:1 | 2:1 | 3:1 | 4:1 |
| Ratio of n- to iso-aldehyde in product | 6.91 | 7.10 | 7.10 | 7.26 |
| 1-Hexene conversion, | 99.9 | 96.9 | 98.7 | 99.4 |
| $k_{obs}$, min$^{-1}$ | 0.136 | 0.018 | 0.018 | 0.016 |
| Percent of reacted hexene converted to: | | | | |
| heptanal | 85.76 | 86.29 | 86.20 | 86.21 |
| 2-methylhexanal | 12.41 | 12.16 | 12.14 | 11.88 |
| 2-hexene | 1.26 | 0.99 | 0.88 | 0.95 |
| hexane | 0.57 | 0.56 | 0.78 | 0.96 |

EXAMPLE IV

By way of comparison with the foregoing, the following table illustrates results which were obtained in a series of runs in which there was employed, as ligand, the triphenylphosphine which is characteristic of much of the prior art. Procedures were the same as in Example I above, with the exception that the only ligand species present was triphenylphosphine, 0.2 millimoles of rhodium was present in each run, 80 ml of toluene were used as liquid reaction medium, and reaction pressure was about 125 psig. (as indicated previously, reaction pressure is known to have no effect on chemical efficiencies and the distribution of aldehyde isomers in the present improved process so long as it is greater than about 50 psig.). The triphenylphosphine concentrations as tabulated are the total concentration of triphenylphosphine moiety, including that contained in the originally-charged RhH(CO)(PØ₃)₃.

Operating results obtained in a series of runs in which the phosphorus:rhodium mole ratio varied between 3 and 285 are as follows:

TABLE IV
USE OF TRIPHENYLPHOSPHINE (TPP) AS LIGAND AT VARYING RATIOS OF TPP TO RHODIUM

Basis: Catalyst is RhH(CO)(PØ₃)₃. Rhodium concentration is 2.0 millimolar in all cases, TPP concentrations as shown. Reaction solvent is 80 cc of toluene. Temperature in each run is 108°–111° C. Pressure of 1:1 hydrogen:CO synthesis gas is 125 ± 1 psig in all cases. Reactant olefin is 20 cc of 1-hexene in all cases. Operating procedures as in preceding examples.

|  | Run No. | | | |
| --- | --- | --- | --- | --- |
|  | 22903-8 | 22903-18 | 22903-20 | 22903-24 |
| Grams RhH(CO)(CØ₃)₃ | 0.1836 | 0.1840 | 0.1837 | 0.1840 |
| TPP concentration millimolar | 6 | 106 | 453 | 570 |
| P/Rh mole ratio | 3 | 53 | 227 | 285 |
| 1-Hexene converstion, % | 99.0 | 99.3 | 99.7 | 99.7 |
| Ratio of n- to isoaldehyde in product | 2.82 | 3.52 | 6.55 | 7.61 |
| $k_{obs}$, min$^{-1}$ | 0.0818 | 0.210 | 0.123 | 0.103 |
| Percent of reacted 1-hexene converted to: | | | | |
| heptanal | 61.7 | 73.3 | 82.3 | 83.1 |
| 2-methylhexanal | 21.8 | 20.8 | 12.6 | 10.9 |
| 2-hexene | 16.1 | 5.2 | 4.9 | 5.7 |
| hexane | 0.4 | 0.7 | 0.2 | 0.3 |

It will be seen that at a phosphorus:rhodium mole ratio of 3 (which gave very good results when the present improved diphosphino ligands were used as in the preceding examples) the efficiency of conversion of 1-hexene to heptanal was only 61.7 and that the ratio of normal to iso-aldehyde in the product was only 2.82. At a phosphorus:rhodium mole ratio of 227 the results were still not quite as satisfactory as those which are easily obtained when using the present bidentate ligands at a phosphorus:rhodium mole ratio of 3:1, and it was only by using a phosphorus:rhodium mole ratio of 285:1 that the operating results summarized in the preceding examples I to III were finally equaled (i.e., very slightly exceeded).

The embodiments of the invention in which an exclusive property or privilege is claimed are defined as follows:

1. In the hydroformylation of an ethylenically unsaturated compound having from 2 to about 25 carbon atoms and free of substituent atoms other than oxygen and nitrogen with hydrogen and carbon monoxide in a liquid-phase reaction zone to produce an aldehyde derivative of said ethylenically-unsaturated compound, said hydroformylation being catalyzed by rhodium hydrido carbonyl in complex combination with a diphosphino ligand at a temperature of from about 50° C. to about 200° C. under a combined partial pressure of hydrogen and carbon monoxide of at least about one atmosphere and with the ratio of hydrogen partial pressure to that of carbon monoxide being from about 10:1 to about 1:10, the improvement which comprises:

employing as said diphosphino ligand an optically-inactive cyclic compound which is a member of the group consisting of:

trans-1,2-bis(diphenylphosphinomethyl)cyclopropane;

trans-1,2-bis(diphenylphosphinomethyl)cyclobutane:

trans-1,2-bis(diphenylphosphinomethyl)cyclopentane;

trans-9,10-bis(diphenylphosphinomethyl)-9,10-dihydrophenanthrene;

trans-1,2-bis(diphenylphosphinomethyl)-trans-decalin;

trans-2,3-bis(diphenylphosphinomethyl)-trans-decalin; and trans-1,9-bis(diphenylphosphinomethyl)-trans-decalin.

2. The improvement of claim 1 wherein there are maintained in said reaction zone at least about 1.5 moles of said diphosphino ligand per atom of rhodium.

3. The improvement of claim 2 wherein said ethylenically unsaturated compound is a hydrocarbon.

4. The improvement of claim 2 wherein the ligand is trans-1,2-bis(diphenylphosphinomethyl)cyclobutane.

* * * * *